(12) United States Patent
Chang et al.

(10) Patent No.: US 10,031,426 B2
(45) Date of Patent: *Jul. 24, 2018

(54) METHOD AND SYSTEM FOR OVERLAY CONTROL

(71) Applicant: Taiwan Semiconductor Manufacturing Company, Ltd., Hsin-Chu (TW)

(72) Inventors: Yang-Hung Chang, Taipei (TW); Chih-Ming Ke, Hsinchu (TW); Kai-Hsiung Chen, New Taipei (TW)

(73) Assignee: TAIWAN SEMICONDUCTOR MANUFACTURING COMPANY, LTD., Hsin-Chu (TW)

( * ) Notice: Subject to any disclaimer, the term of this patent is extended or adjusted under 35 U.S.C. 154(b) by 414 days.

This patent is subject to a terminal disclaimer.

(21) Appl. No.: 14/733,300

(22) Filed: Jun. 8, 2015

(65) Prior Publication Data

US 2015/0268564 A1    Sep. 24, 2015

Related U.S. Application Data

(63) Continuation of application No. 14/017,793, filed on Sep. 4, 2013, now Pat. No. 9,053,284.

(51) Int. Cl.
  *G06F 17/50* (2006.01)
  *G06F 19/00* (2018.01)
  (Continued)

(52) U.S. Cl.
  CPC ...... *G03F 7/70633* (2013.01); *G06F 17/5081* (2013.01); *G01N 37/00* (2013.01); *G01P 21/00* (2013.01); *G01R 31/26* (2013.01); *G03F 1/00* (2013.01); *G03F 9/00* (2013.01); *G06F 19/00* (2013.01); *G06F 2217/02* (2013.01); *G06F 2217/06* (2013.01); *G06F 2217/12* (2013.01); *G06F 2217/16* (2013.01); *G21K 5/00* (2013.01); *H01L 21/00* (2013.01)

(58) Field of Classification Search
  CPC .......... G06F 17/16; G06F 17/02; G06F 17/06; G06F 17/5081; G06F 19/00; G03F 9/00; G03F 1/00; G21K 5/00; G01R 31/26; H01L 21/00; G01N 37/00; G01P 21/00
  USPC .............. 716/54, 55, 56, 136; 700/109, 121; 702/83, 94; 438/16, 800; 378/34, 35; 430/4, 22
  See application file for complete search history.

(56) References Cited

U.S. PATENT DOCUMENTS 6,603,529 B1    8/2003    Finarov
6,948,149 B2    9/2005    Goodwin
(Continued)

*Primary Examiner* — Phallaka Kik
(74) *Attorney, Agent, or Firm* — Haynes and Boone, LLP

(57) ABSTRACT

A method for overlay monitoring and control is introduced in the present disclosure. The method includes selecting a group of patterned wafers from a lot using a wafer selection model; selecting a group of fields for each of the selected group of patterned wafers using a field selection model; selecting at least one point in each of the selected group of fields using a point selection model; measuring overlay errors of the selected at least one point on a selected wafer; forming an overlay correction map using the measured overlay errors on the selected wafer; and generating a combined overlay correction map using the overlay correction map of each selected wafer in the lot.

20 Claims, 14 Drawing Sheets

(51) Int. Cl.
  *G03F 9/00* (2006.01)
  *G03F 1/00* (2012.01)
  *G21K 5/00* (2006.01)
  *G01R 31/26* (2014.01)
  *G01N 37/00* (2006.01)
  *G01P 21/00* (2006.01)
  *H01L 21/00* (2006.01)
  *G03F 7/20* (2006.01)

(56) References Cited

U.S. PATENT DOCUMENTS

| | | | |
|---|---|---|---|
| 7,349,752 B1 | 3/2008 | Sturtevant et al. | |
| 8,867,018 B2 | 10/2014 | Lu et al. | |
| 9,052,709 B2 * | 6/2015 | Cohen | G05B 19/41875 |
| 9,053,284 B2 * | 6/2015 | Chang | G06F 17/5081 |
| 9,291,911 B2 * | 3/2016 | Dishon | G03F 7/3028 |
| 9,347,879 B2 * | 5/2016 | Adel | G03F 7/70633 |
| 9,620,426 B2 * | 4/2017 | Izikson | H01L 22/20 |
| 2002/0105649 A1 * | 8/2002 | Smith | G03F 7/70558 356/401 |
| 2004/0233442 A1 | 11/2004 | Mieher et al. | |
| 2005/0188342 A1 | 8/2005 | Goodwin | |
| 2009/0284744 A1 | 11/2009 | Mieher et al. | |
| 2010/0284008 A1 * | 11/2010 | Coene | G03F 7/70633 356/401 |
| 2011/0202298 A1 | 8/2011 | Izikson et al. | |
| 2011/0205515 A1 * | 8/2011 | Menchtchikov | G03B 27/53 355/67 |
| 2012/0029856 A1 | 2/2012 | Cohen et al. | |
| 2012/0208301 A1 | 8/2012 | Izikson et al. | |
| 2013/0293872 A1 | 11/2013 | Dishon et al. | |
| 2014/0017604 A1 * | 1/2014 | Lee | G03F 7/70633 430/30 |
| 2014/0036243 A1 * | 2/2014 | Beyer | G03F 1/72 355/52 |
| 2014/0320837 A1 | 10/2014 | Dishon et al. | |
| 2015/0067617 A1 | 3/2015 | Chang et al. | |
| 2016/0047744 A1 * | 2/2016 | Adel | G03F 7/70633 356/401 |

* cited by examiner

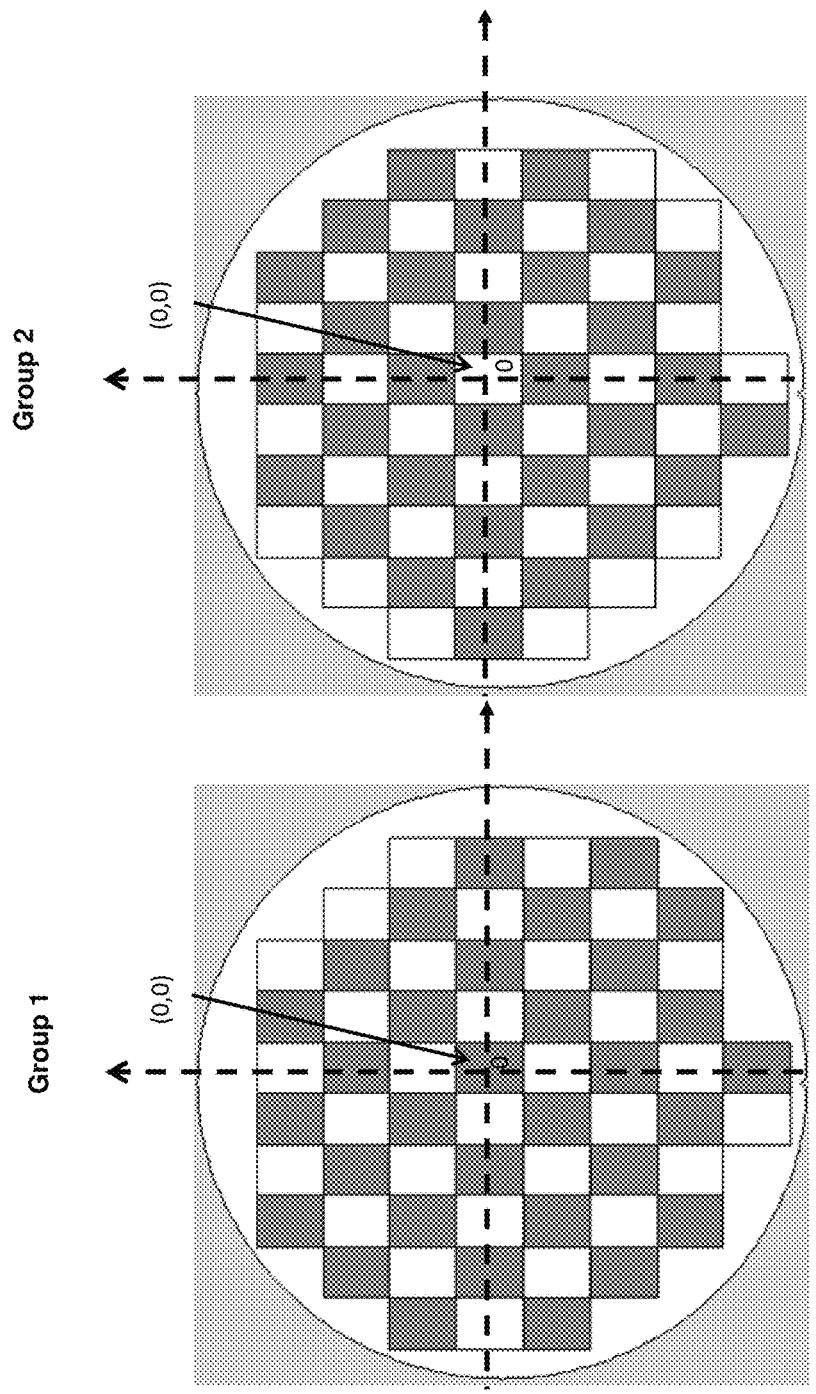

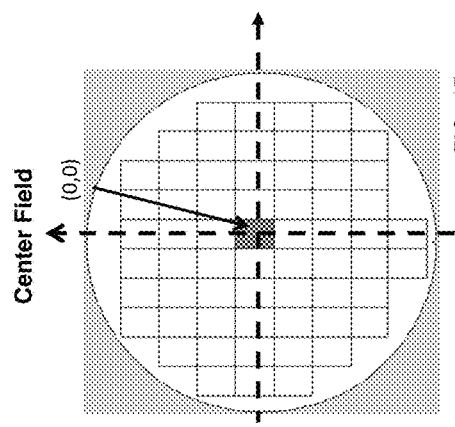
FIG. 4A Edge Fields
FIG. 4C Group A
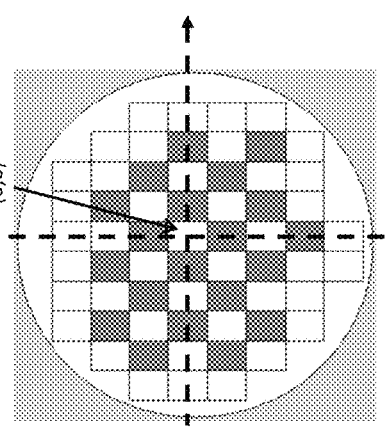
FIG. 4B Center Field
FIG. 4D Group B

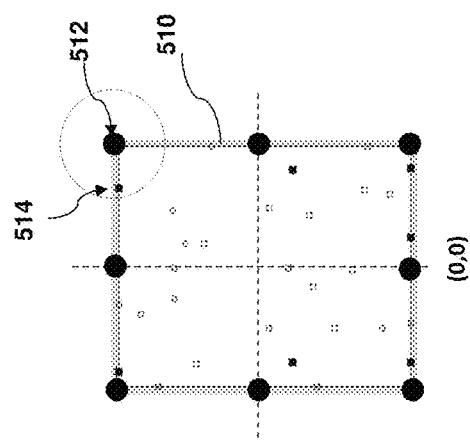
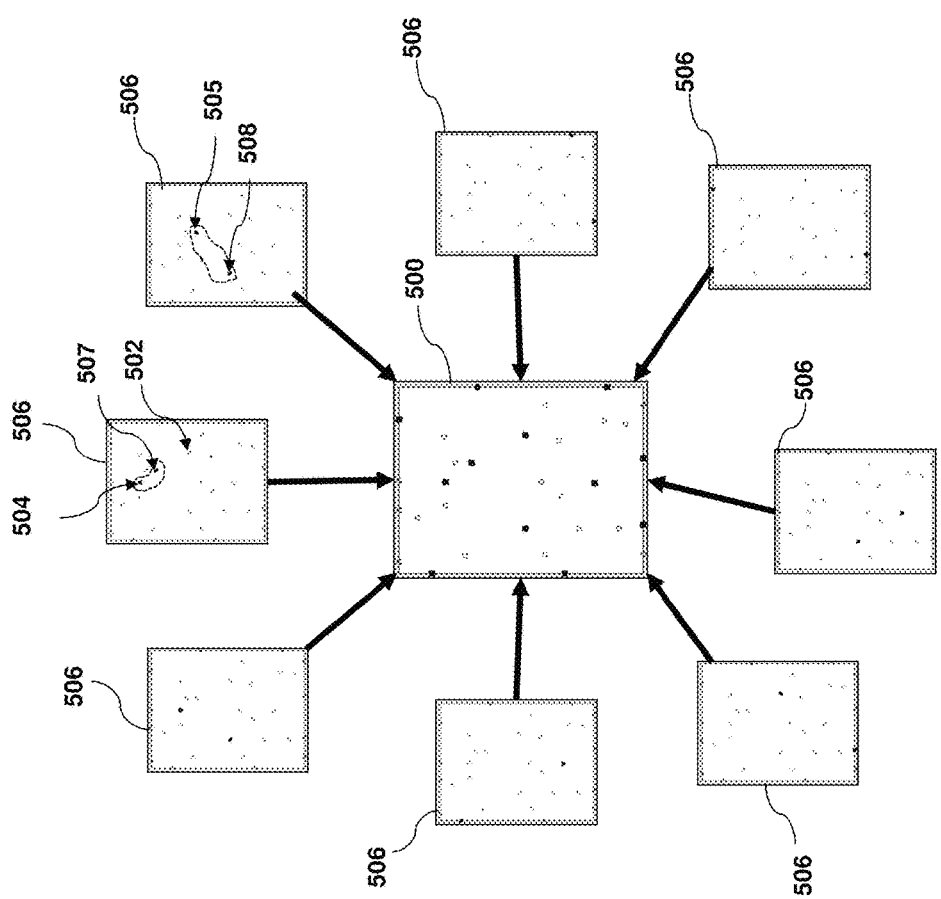

METHOD AND SYSTEM FOR OVERLAY CONTROL

PRIORITY DATA

The present application is a continuation application of U.S. patent application Ser. No. 14/017,793 filed Sep. 4, 2013, entitled "METHOD AND SYSTEM FOR OVERLAY CONTROL," which is hereby incorporated by reference in its entirety.

BACKGROUND

The semiconductor integrated circuit (IC) industry has experienced exponential growth. Technological advances in IC materials and design have produced generations of ICs where each generation has smaller and more complex circuits than the previous generation. In the course of IC evolution, functional density (i.e., the number of interconnected devices per chip area) has generally increased while geometry size (i.e., the smallest component (or line) that can be created using a fabrication process) has decreased. This scaling down process is the result of various process changes and improvements, including more precise lithography. Such scaling down has also increased the complexity of processing and manufacturing ICs and, for these advances to be realized, similar developments in IC processing and manufacturing are needed.

With small feature sizes in advanced technology nodes, lithography patterning faces more challenges. For example, overlay error needs to be much smaller since feature size is reduced. On the other hand, lithography technology uses a radiation beam of high energy photons, such as deep ultraviolet (DUV) or extreme ultraviolet (EUV), since high energy photons have short wavelength and high resolution that enable formation of small size features.

The method for overlay control and monitoring usually includes selecting limited number of sample wafers by an experienced user and measuring only the selected sample wafers. The sampling locations and quantities on each selected wafers are also decided by the user. For example, 17 dies out of 62 dies on a wafer, and 12 points out of each selected die are decided by the user's experience for performing the overlay error measurement. This method relies on human experience, thus sometimes results in poor measurement coverage, such as full measurement in some fields and no measurement in other fields. This method may also introduce redundant measurements in some regions of the wafer which result in inefficient and ineffective processes and low throughput. Therefore there is a need for an optimized sampling strategy for overlay control and monitoring.

BRIEF DESCRIPTION OF THE DRAWINGS

The present disclosure is best understood from the following detailed description when read with accompanying figures. It is emphasized that, in accordance with the standard practice in the industry, various features are not drawn to scale and are used for illustration purpose only. In fact, the dimension of the various features may be arbitrarily increased or reduced for clarity of discussion.

FIGS. 3A-3B illustrate a method of dividing the fields of a wafer according to various embodiments of the present disclosure.

FIGS. 4A-4F illustrate a method of dividing the fields of a wafer according to various embodiments of the present disclosure.

FIG. 5A illustrates a combined intra-field overlay map of point selection processes performed in the same field on a plurality of wafers according to some embodiments of the present disclosure.

FIG. 5B is an exemplary method of point selection process performed in the center field according to some embodiments of the present disclosure.

DETAILED DESCRIPTION

Figure 1A:
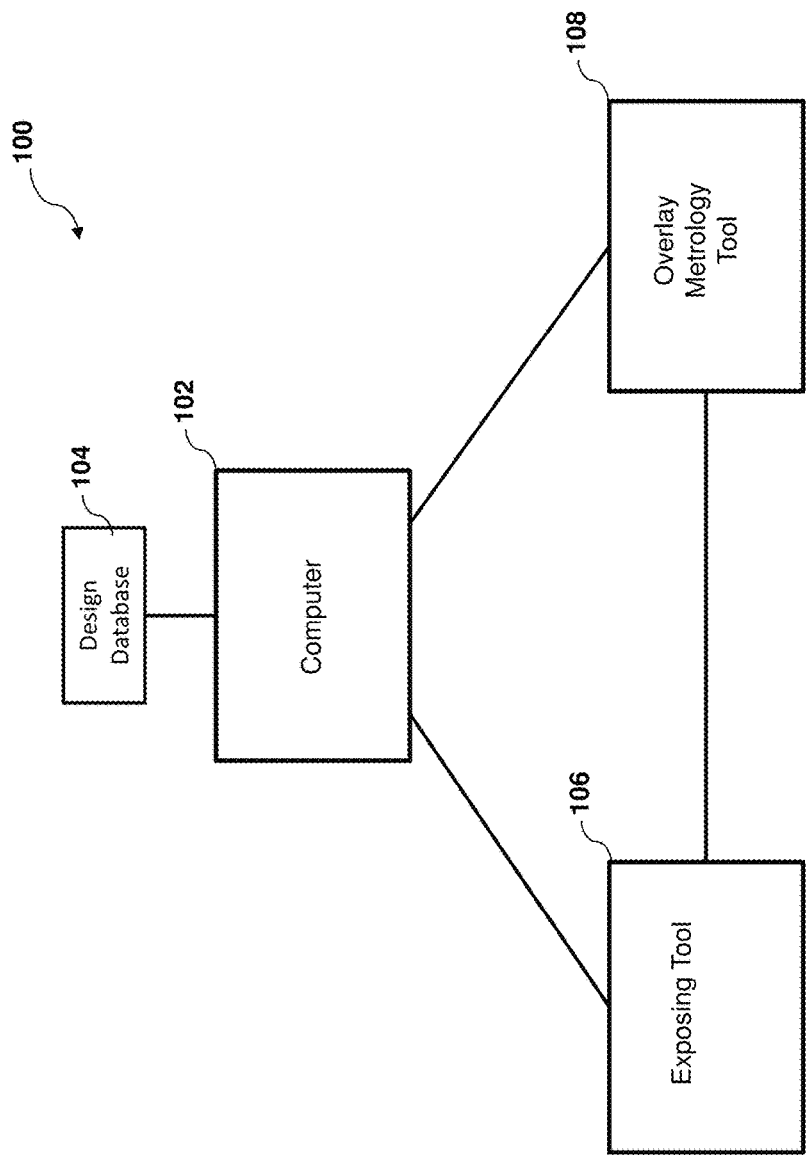
FIG. 1A is a block diagram of a system for overlay control and monitoring constructed according to various embodiments of the present disclosure.

The following disclosure provides many different embodiments, or examples, for implementing different features of the disclosure. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

FIG. 1A is a block diagram illustrating a system 100 for implementing a method for overlay control and monitoring according to various aspects of the present disclosure. It is understood that other configurations and inclusion or omission of various items in the system 100 may be possible. The system 100 is exemplary, and is not intended to limit the disclosure beyond what is explicitly recited in the claims. As shown in FIG. 1A, the system 100 includes a computer 102, an exposing tool 106, and an overlay metrology tool 108.

Referring to FIG. 1A, the system 100 includes a computer 102. In some embodiments, the computer 102 may generate one or more selection models for selecting points, fields, and/or wafers in one or more lots for overlay errors measurement and control. The computer 102 may also perform statistical analysis of the collected overlay error data, for example, the computer 102 may weight the points, fields, and/or wafers based their possibility of being chosen using the overlay error data from the previous measurements. The computer 102 may generate a combined overlay correction map based on the overlay error data measured from a plurality of wafers in one lot, or in a plurality of lots on a run-to-run basis. In some embodiments, the computer 102 is a standard, general-purpose computer, including a processor, memory, and an interface. The computer 102 may be a single computer or a distributed computer, and connects to various components of the exposing tool 106 and overlay metrology tool 108, including but not limited to the connections shown in FIG. 1A. In some embodiments, the computer 102 includes one or more software programs for calculating and predicting overlay data.

In an alternative embodiment, the system 100 may also include an integrated circuit (IC) design database 104 coupled to the computer 102. The IC design database 104 is designed to store and manage IC design layout data. In some embodiments, the IC design database 104 includes a plurality of IC design layouts which will be transferred onto a semiconductor wafer to form various circuit components. The circuit components may include a transistor, a capacitor, a resistor, and/or a metal line connecting the IC devices. An IC design layout includes an IC pattern having a plurality of IC features. The IC pattern is formed on a mask. In a lithography process, the IC pattern (with the IC features) is transferred to a resist layer coated on the wafer using the mask and the exposing tool 106. In some embodiments, the design database may be integrated in the computer 102.

In some embodiments, the computer 102 calculates and predicts one or more process parameters for evaluating the exposure process. The process parameters may be determined using information from the design database 104 and the exposing tool 106. The process parameters may be used to determine the number and positions of the overlay marks that are patterned on the mask and then transferred onto the resist pattern of the IC design on the wafer during exposure. The overlay errors may be calculated by comparing the positions of the predetermined overlay marks and the corresponding marks on the resist pattern formed during exposure. The overlay errors of different wafers from one or more lots may be combined to form an overlay correction map. The combined overlay correction map may demonstrate a model including compensation values that are needed to adjust the exposure tool 106 so that the overlay error may be reduced in the future exposure process. For example, the model may be a linear model showing a linear increasing or decreasing trend along a certain direction. The exposure tool 106 may be adjusted to compensate for the previously discovered trend.

The exposing tool 106 of FIG. 1A is further described in detail with reference to FIG. 1B in a schematic view. The exposing tool 106 is operable to expose a resist layer coated on a wafer 164. In some embodiments, the exposing tool 106 includes a radiation source (illumination source) 152 to generate radiation energy (or radiation beam) to expose the resist layer. The radiation energy includes ultraviolet (UV) light, deep ultraviolet (DUV) light, extreme ultraviolet (EUV) light, electron-beam in various examples.

The exposing tool 106 may also include an illumination module with various optical components configured to image a mask 158 onto a wafer 164. The illumination module may include multiple lenses and/or other optical components. In some embodiments as shown in FIG. 1B, the illumination module includes a lens 154 and a projection lens 160.

The exposing tool 106 may also include a mask stage 156 designed to secure a mask (also referred to as reticle or photo mask) 158 and configured between the lens 154 and a projection lens 160. The mask 158 has a pattern to be transferred to the semiconductor wafer 164. The pattern of the mask 158 may include a plurality of predetermined overlay marks used in the following overlay control and monitoring process. In some embodiments, the mask 158 includes a substrate and a patterned layer formed on the substrate. In some embodiments, the mask 158 includes a transparent substrate and a patterned absorption layer. The transparent substrate may use fused silica ($SiO_2$) relatively free of defects, such as borosilicate glass and soda-lime glass. The transparent substrate may use calcium fluoride and/or other suitable materials. The patterned absorption layer may be formed using a plurality of processes and a plurality of materials, such as depositing a metal film made with chromium (Cr), or other suitable material, such as MoSi. A light beam may be partially or completely blocked when directed on an absorption region. The absorption layer may be patterned to have one or more openings through which a light beam may travel without being absorbed by the absorption layer. The mask may incorporate other resolution enhancement techniques such as phase shift mask (PSM) and/or optical proximity correction (OPC).

In some embodiments, the mask 158 is a reflective mask used in an EUV lithography system. The reflective mask includes a substrate of a low thermal expansion material (LTEM), and a reflective multilayer film formed on the substrate. The reflective mask further includes an absorption layer patterned to form a main pattern according to an IC design layout.

The exposing tool 106 also includes a wafer stage 162 designed to secure a wafer 164 and is operable to move transitionally and/or rotationally. The wafer 164 may be a semiconductor wafer, such as a silicon wafer, or other suitable wafer to be patterned.

Still referring to FIG. 1A, the system 100 includes an overlay metrology tool 108 coupled with the exposing tool 106 and the computer 102. The overlay metrology tool 108 is designed to measure overlay error data between the predetermined positions of the overlay marks and the positions of the marks transferred onto the resist pattern on the wafer during the exposure process. The overlay metrology tool 108 receives the wafer with the resist pattern, performs an overlay measurement of the resist pattern to obtain the overlay error data of the resist pattern, and may send the overlay error data to the computer 102 for further processing.

The overlay error data of a plurality of wafers may be used for generating a combined overlay correction map to evaluate and adjust the exposure condition of the exposure tool 106 when necessary. The system 100 is described according to various embodiments. However, in various embodiments, the various modules of the system 100 may be integrated together. For example, although FIG. 1 illustrates an overlay metrology tool 108 separate from the exposing tool 106, the overlay metrology tool 108 may be integrated into the exposing tool 106 in any suitable configuration. In some embodiments, the various modules of the system 100 may be distributed in different locations and coupled together through intranet or the internet. In some embodiments, various functions may be built in different modules. For example, the one or more selection models may be generated by the computer 102 or the overlay metrology tool 108.

Figure 1B:
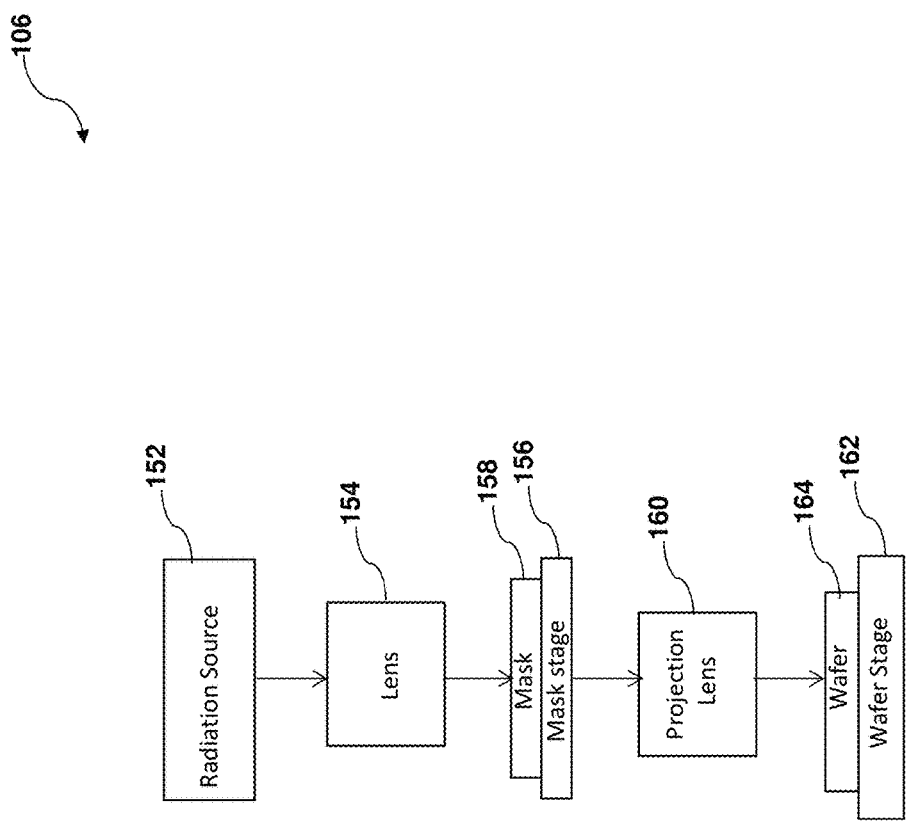
FIG. 1B is a schematic diagram of an exposing tool constructed according to various embodiments of the present disclosure.
Figure 2A:
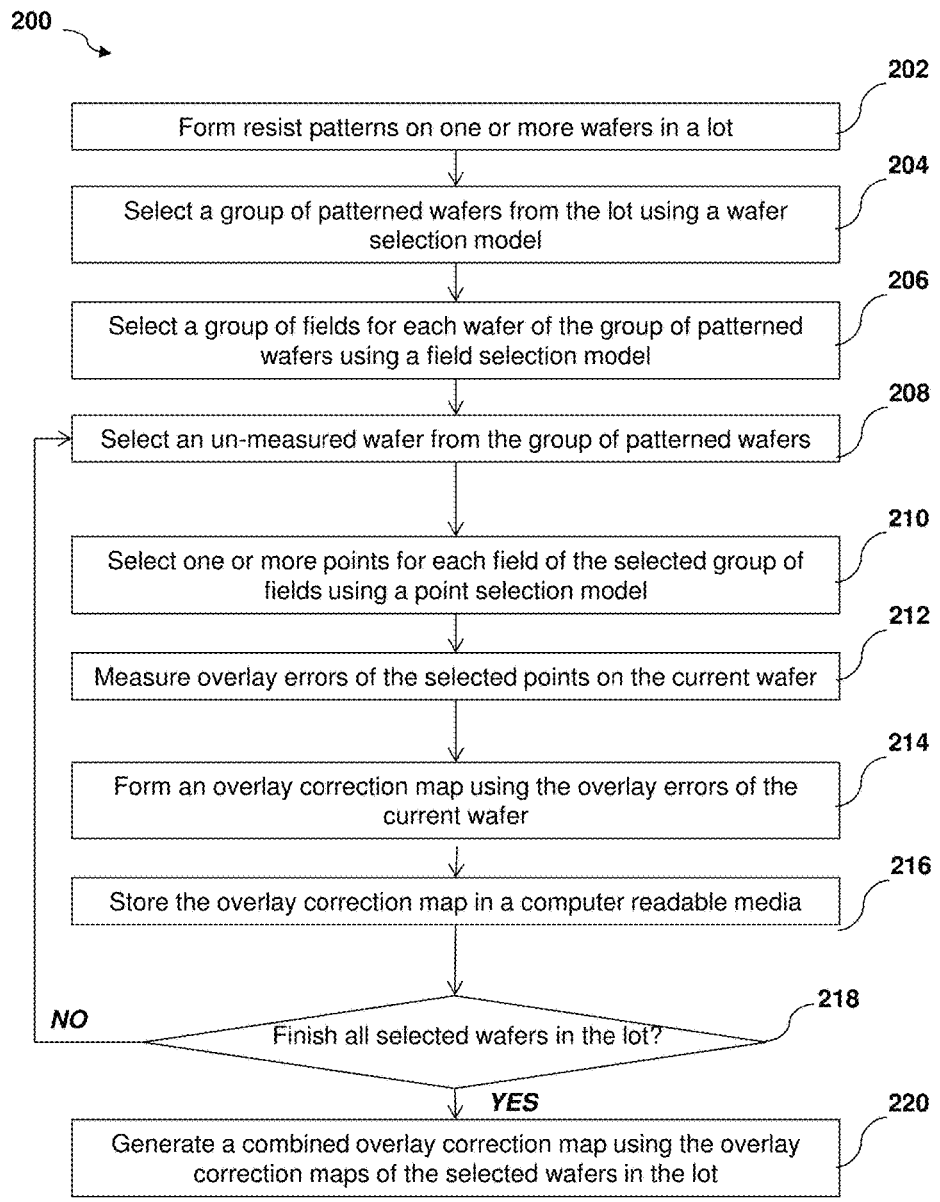
FIG. 2A is a flowchart of a method for overlay control and monitoring using the system of FIG. 1A according to various embodiments of the present disclosure.

FIG. 2A is a flowchart of a method 200 for forming a combined overlay correction map for overlay control and monitoring according to various embodiments of the present disclosure. In some embodiments, the method 200 is implemented using the system 100 as shown in FIGS. 1A-1B. It is understood that additional steps can be provided before, during, and after the method 200, and some steps described can be replaced, eliminated, or moved around for additional embodiments of the method 200. The method 200 is an example, and is not intended to limit the disclosure beyond what is explicitly recited in the claims.

The method 200 begins at operation 202 by forming resist patterns on one or more wafers 164 in a lot using the exposing tool 106. In some embodiments, the wafers 164 include a silicon wafer. Alternatively or additionally, the wafers 164 include another elementary semiconductor, such as germanium; a compound semiconductor including silicon carbide, gallium arsenic, gallium phosphide, indium phosphide, indium arsenide, and/or indium antimonide; or an alloy semiconductor including SiGe, GaAsP, AlInAs, AlGaAs, GaInAs, GaInP, and/or GaInAsP. In various embodiments, the wafers 164 may include a plurality of circuit features, such as an isolation feature, a doped well, a source/drain, a gate, a via feature or a metal line.

Still referring to operation 202, the resist patterns may be formed on the wafers 164 using a lithography process. In some embodiments, the lithography process may include forming a resist layer overlaying the wafer 164, exposing the resist layer to a pattern on the mask, performing a post-exposure bake process, and developing the resist layer to form a masking element including the resist layer on the wafer. In some embodiments, the mask includes a plurality of predetermined overlay marks. Therefore, the resist patterns formed on the wafer may also include a plurality of marks corresponding to the overlay marks formed during the exposure process.

At operation 204 of method 200, a group of pattered wafers from a lot are selected for overlay error measurement. The wafer selection process may be performed by the overlay metrology tool 108, using a wafer selection model generated by the computer 102. In general, there are a plurality of wafers in one lot, for example, 25 wafers in one lot. The wafers within a lot may be selected randomly to be measured. The number of wafers to be chosen in a lot may be predetermined depending on the amount of data needed to generate the overlay correction map with optimized coverage to better evaluate the process parameters. Meanwhile, the number of wafers is also chosen in consideration of the amount of time needed for the overlay measurement in a lot. In some examples, 6-12 pieces of wafers in a lot may be selected for overlay error measurement.

In some examples, the wafer selection model includes selecting a group of wafers with each wafer positioned at a constant interval from each other within a lot. For example, the group of wafers may include wafers positioned at odd number sequence (e.g., $1^{st}$, $3^{rd}$, $5^{th}$, . . . ), or even number sequence (e.g., $2^{nd}$, $4^{th}$, $6^{th}$, . . . ) within a lot.

The wafer selection model, in some embodiments, includes weighting the possibilities of each wafer location (e.g., sequence $1^{st}$, $2^{nd}$, $3^{rd}$ . . . ) within a lot of being chosen based on the data from the previous overlay measurements. The wafer selection model then selects the patterned wafers in the locations with less possibilities of being chosen previously. For example, the wafer locations within a lot may be weighted by using a weighting factor $x_{ij}$ to indicate the possibility of the wafer at the corresponding location being chosen based on the previous selections and measurements data, wherein $x_{ij}$ indicates the weighting factor of a patterned wafer at wafer location i being chosen for j times in the previous overlay measurements. Each wafer location is assigned with an initial weighting factor $x_{i0}$=100%, indicating a patterned wafer at wafer location i being chosen for zero times in the previous overlay measurements. After a patterned wafer at wafer location i is selected once in the history, the weighting factor $x_{ij}$ is multiplied by a predetermined factor, such as a=0.5. Then the current weighting factor of a patterned wafer at wafer location i becomes $x_{i1}=x_{i0} \cdot a=50\%$, indicating a decreased possibility, e.g., from 100% to 50%, of being chosen for future overlay error measurements. Accordingly the weighting factor $x_{ij}$ may change based on the times of being selected and measured in the previous overlay measurements. The weighting factor $x_{ij}$ of the patterned wafer may be then used in the wafer selection models to select one or more patterned wafers within a lot in the current wafer selection process. For example, the patterned wafer with the largest weighting factor $x_{ij}$ may have the least possibility of being chosen in the previous overlay error measurements, and thus may be most likely to be selected for the current overlay error measurement. The above mentioned embodiments are merely exemplary, and are not intended to limit the disclosure beyond what are explicitly listed.

Figure 2B:
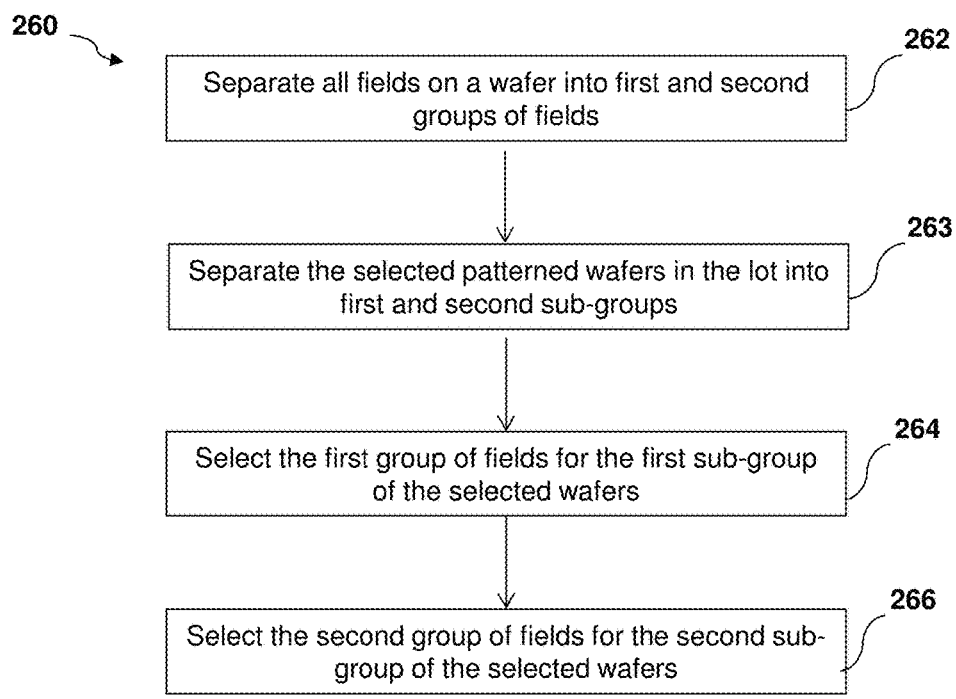
FIG. 2B is a flowchart illustrating an example of field selection model according to some embodiments of the present disclosure.

The method 200 proceeds to operation 206 by selecting a group of fields on each selected patterned wafer for overlay error measurement by the overlay metrology tool 108, based on a field selection model generated by the computer 102. In some embodiments, a wafer may be divided into a plurality of fields for overlay error measurement as shown in FIGS. 3A-3B and 4A-4F. The fields on a wafer may be dies on the wafer. FIG. 2B is a flowchart showing an example of field selection model 260 performed at operation 206.

Referring to FIGS. 3A-3B, in some examples, the fields on a wafer may be separated into a first group (as shown in FIG. 3A) and a second group (as shown in FIG. 3B). One example of separating the first group from the second group of fields may be described as follows. A two dimensional frame may be used as a coordination system to label the position of each field on a wafer. The origin of the two dimensional frame may be put in a predetermined field in the middle region of the wafer, as shown in FIGS. 3A-3B. In one example, the field (0, 0) may be included in the first group. The fields to the next right, next left, next up and next down of the field (0, 0) are also included in the first group. The rest of the fields in the first group may be selected in the similar method where no two immediately adjacent fields are included in the first group. The fields to the immediate right, immediate left, immediate up and immediate down of the (0, 0) field are included in the second group. The rest of the fields in the second group may be selected in the similar method where no two immediately adjacent fields are included in the second group. In some embodiments, the first group of fields is a complement set of the second group of fields, where there is common field owned by both first and second groups, and the sum of the first and second groups of fields can cover the entire fields on a wafer.

Figure 4E:
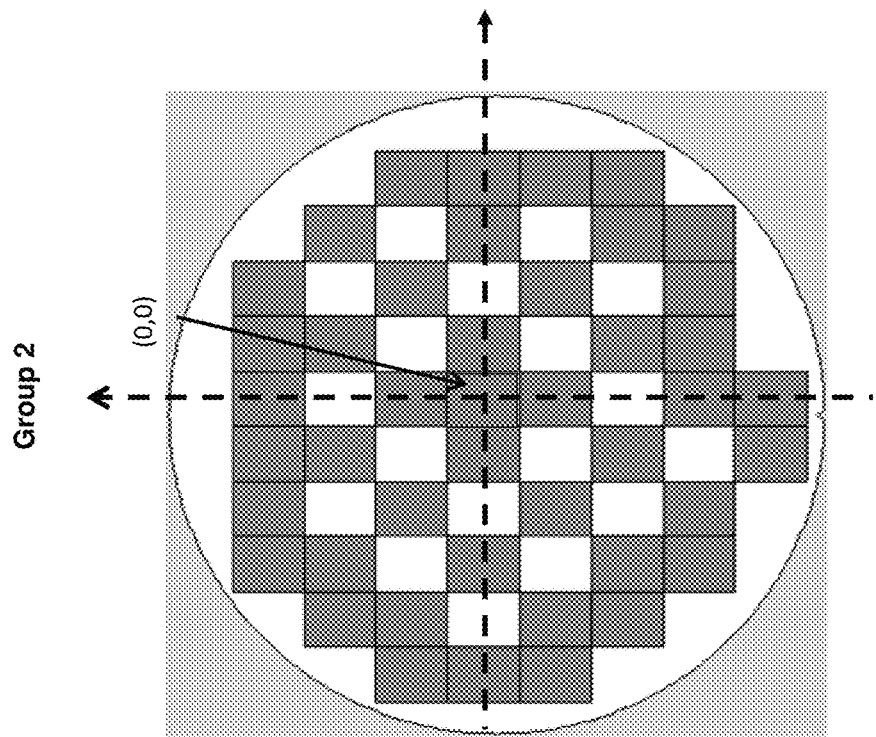
Figure 4F:
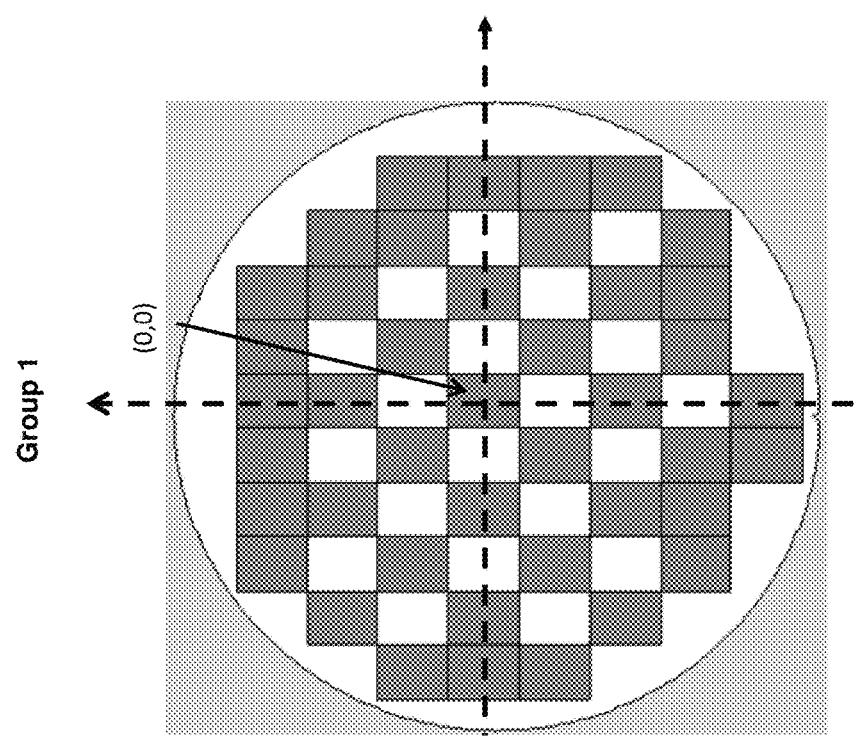

Referring to FIGS. 4A-4F, in some embodiments, the fields may be separated using an alternative method. For example, the fields disposed at the edges of the wafer are defined as edge fields (EF) as shown in FIG. 4A. The field disposed at the origin (0, 0) of the two dimensional frame is defined as a center field (CF) as shown in FIG. 4B. The rest of the fields on the wafer can be separated into first and second types of fields using similar method as described with respect to FIGS. 3A-3B. For example, the origin field (center field) is included in the first type of fields, and the fields that are disposed to the next right, next left, next up and next down are also included in the first type of fields. The first type of fields also includes fields that are disposed not immediately next to each other as shown in FIG. 4C. The fields to the immediate right, immediate left, immediate up and immediate down of the (0, 0) field are included in the second type of fields. The second type of fields may be selected in the similar method where no two immediately adjacent fields are included in the second type of fields, as shown in FIG. 4D. All of the fields on a wafer may be then separated into first and second groups as shown in FIGS. 4E-4F. The first group of fields includes edge fields, center field, and the first type of fields as shown in FIG. 4E. The second group of fields includes edge fields, center field, and the second type of fields as shown in FIG. 4F.

At operation 206 for overlay error measurement, the field selection process may be performed by the overlay metrology tool 108. After all the fields have been separated into the first and second groups as shown in step 262 of FIG. 2B, the field selection model 260 of operation 206 may proceed to step 263 by separating the selected group of patterned wafers in the lot from operation 204 into first and second sub-groups of wafers. In some embodiments, the first and second sub-groups of wafers are randomly divided to have the same or not the same number of wafers. In some embodiments, the first and second sub-group may be assigned to the selected patterned wafers in an alternating sequence. The field selection model 260 then proceeds to selecting the first group of fields for the first sub-group of wafers to be tested (step 264 of method 260), and selecting the second group of fields for the second sub-group of wafers to be tested (step 266 of method 260). Although the fields on a wafer are only described to be separated into two groups in the current disclosure, the fields may be divided into any suitable number of groups in any suitable topology, for example n groups. The selected patterned wafers may be also divided into m sub-groups, where each of the n groups of fields is assigned to each of the m sub-groups of wafers to be tested. The number of the sub-groups m may or may not equal to the number n of categories of the fields.

Still referring to operation 206, the field selection model may also include some alternative methods. In some embodiments, the field position on a wafer may be weighted using a weighting factor to indicate the possibility of the field at the corresponding location being chosen based on the previous selections and measurements data. The field with a less possibility of being chosen in the previous measurement may have a higher possibility of being selected for the current overlay error measurement. The detailed weighting and selecting process may be similar to the examples of wafer selection models as discussed with respect to operation 204 of method 200. The above mentioned embodiments are exemplary, and are not intended to limit the disclosure beyond what are explicitly listed.

Referring to FIG. 2A, method 200 proceeds to operation 208 by selecting an un-measured wafer of the selected group of patterned wafers.

Referring to FIGS. 2A and 5A, method 200 proceeds to operation 210 by selecting at least one point (e.g., point 504, 507, 505 or 508) among the marks (e.g., 502) transferred from overlay marks in a field (e.g., field 506) selected from operation 206 to measure overlay errors by the overlay metrology tool 108. At least one point is selected for each field of the group of fields selected at operation 206. The marks 502 may be determined using the process parameters, and then patterned on the mask 158. Marks 502 corresponding to the overlay marks on the mask 158 are then formed on the resist pattern on the wafer 164 using the mask 158 during exposure. The point selection process may be performed based on a point selection model generated by the computer 102.

In some embodiments, the point selection model includes randomly selecting a first group of points (e.g., points 504 and 507) among the marks transferred from the overlay marks (e.g., overlay mark 502) in a field 506, wherein the field 506 is selected from operation 206 on a wafer out of the first sub-group of wafers. A second group of points (e.g., points 505 and 508) are then selected among the marks transferred from the overlay marks (e.g., overlay mark 502) in the field 506 on a different wafer out of the first sub-group of wafers. In some embodiments, the first group of points is different from the second group of points. In some embodiments, the first group of points is the same as the second group of points. The number of wafers in each sub-group and/or the number of points selected in each field are predetermined to have an optimized relationship between the number of marks being tested and the time needed for scanning among all selected wafers. Referring to FIGS. 5A-5B, in some embodiments, there are two points being selected each time in a field. In some alternative embodiments, one point or more than two points may be selected in a field to determine the overlay errors.

In some alternative embodiments, all the marks transferred from the overlay marks (e.g., overlay mark 502) onto the resist pattern within a field (e.g., field 506) may be weighted by their possibility of being chosen based on the previous selections and measurements data. Then one or more points with less possibilities of being chosen in the previous measurements are selected for the current overlay error measurement. The detailed weighting and selecting process may be similar to the examples of wafer selection models as discussed with respect to operation 204 of method 200. The above mentioned embodiments are exemplary, and are not intended to limit the disclosure beyond what are explicitly listed.

During the exposure process, center field may have greater overlay shift due to the lens heating and reticle heating. Therefore, during overlay measurement, center field (0, 0) may have a different point selection method from the rest of the fields on a wafer. In some examples, as shown in FIG. 5B, eight fixed points (e.g., point 512) may be selected to calculate the overlay errors for center field (0, 0) 510. A closest point (e.g., point 514) to a fixed point (e.g., point 512) may be selected to calculate the overlay errors.

Figure 5C:
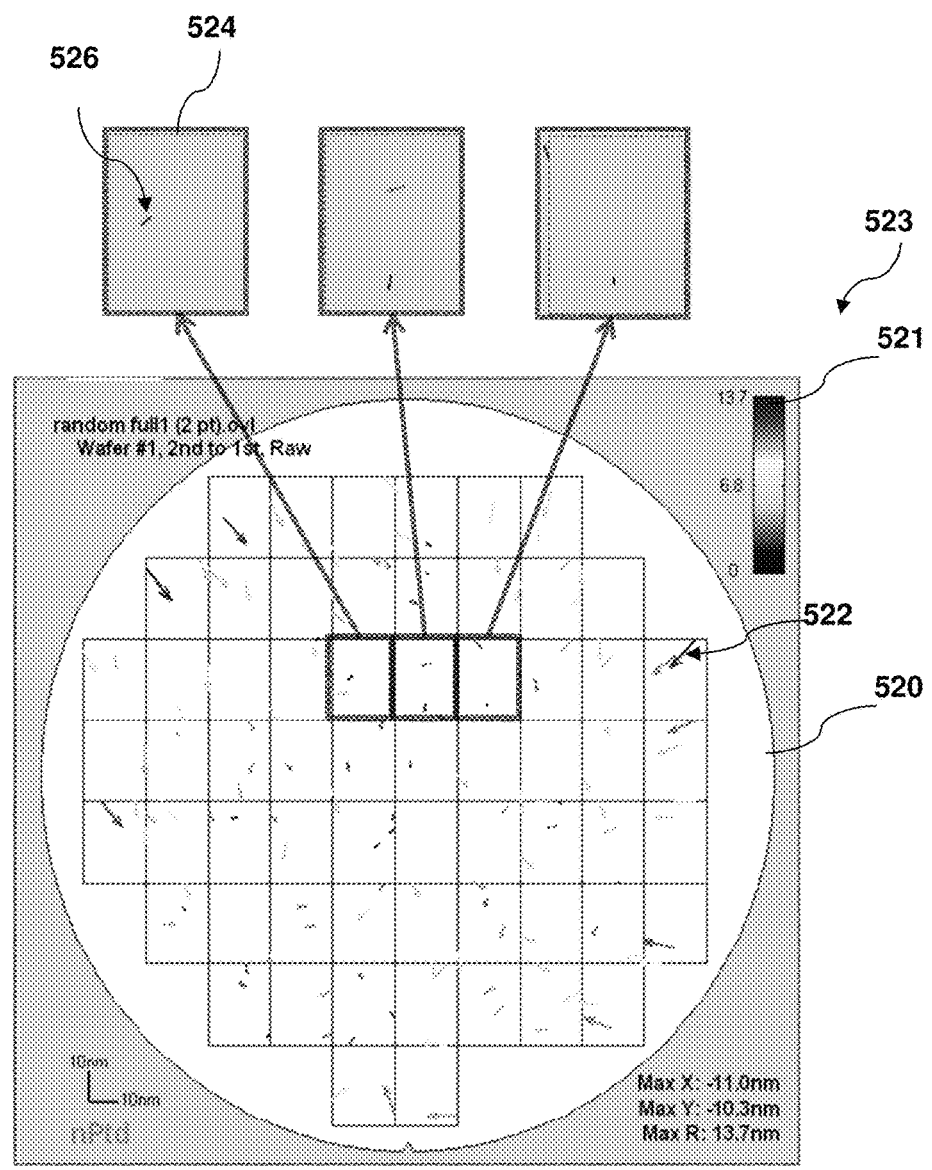
FIG. 5C is an overlay correction map formed using the overlay errors measured on a wafer according to some embodiments of the present disclosure.

Referring to FIGS. 2 and 5C, method 200 proceeds to operation 212 by measuring the overlay error of the selected points on the current wafer at operation 210. The overlay errors may be determined by checking if the positions of the selected points on the resist pattern match with the positions of the corresponding overlay marks transferred onto the resist pattern. When there is a position difference between the selected points and the corresponding overlay marks, the overlay errors may be represented using the vectors (e.g., vector 522 in FIG. 5C) illustrating the position difference and direction difference between the selected points and the corresponding overlay marks. The different grey levels of colors of the arrow vectors show in FIG. 5C reflect the magnitude of the values of overlay errors as shown in the scale 521.

Method 200 proceeds to operation 214 by forming an overlay correction map (e.g., 523 of FIG. 5C) of the measured overlay errors on the current wafer from operation 212. FIG. 5C shows an overlay correction map 523 formed using the overlay errors measured on a wafer 520. The overlay error correction map may be constructed by the overlay error vectors, such as overlay error vectors 522 and 526. The overlay error vectors may be formed by comparing, on a point-to-point basis, the measured positions of the selected points and the positions of the corresponding overlay marks. In some examples, the field coverage rate by the selected points using the point selection model and field selection model of the present disclosure may be around 30% on a wafer (e.g., wafer 520).

Method proceeds to operation 216 by storing the overlay correction map of the current wafer in a computer readable media on the computer 102. Some common forms of computer readable media includes, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, carrier wave, or any other medium from which a computer is adapted to read.

Method 200 proceeds to operation 218 to decide if all wafers selected from operation 204 have been measured. When not all selected wafers have been measured, method 200 proceeds to operation 208 by selecting the next unmeasured wafer from the selected group of patterned wafers. Operation 208 then proceeds to operations 210-216 to measure the overlay errors of the next wafer and form an overlay correction map of the next wafer. The formed overlay correction map is stored in the computer readable media.

FIG. 5A shows a combined intra-field overlay map 500 illustrating the point selection processes performed in the same field 506 on different wafers. A plurality of marks (e.g., mark 502) are patterned in field 506 on a plurality of different wafers. The point selection processes may select different points, for example points 504 and 507 in field 506 on a first wafer, and points 505 and 508 on a second wafer, using the point selection model for overlay error measurement. A plurality of wafers with selected points in field 506 are combined to form a combined intra-field overlay map 500 corresponding to the overlay error distribution in field 506. As shown in FIG. 5A, although only a certain number of points in field 506 on each wafer are selected for overlay error measurement, after combining the overlay error data from a plurality of wafers, the measured points in field 506 may have a good coverage of all the marks. For example the field coverage rate by the measured points using the point selection model and field selection model of the present disclosure may be around 50% for all the selected wafers in a lot.

Figure 6A:
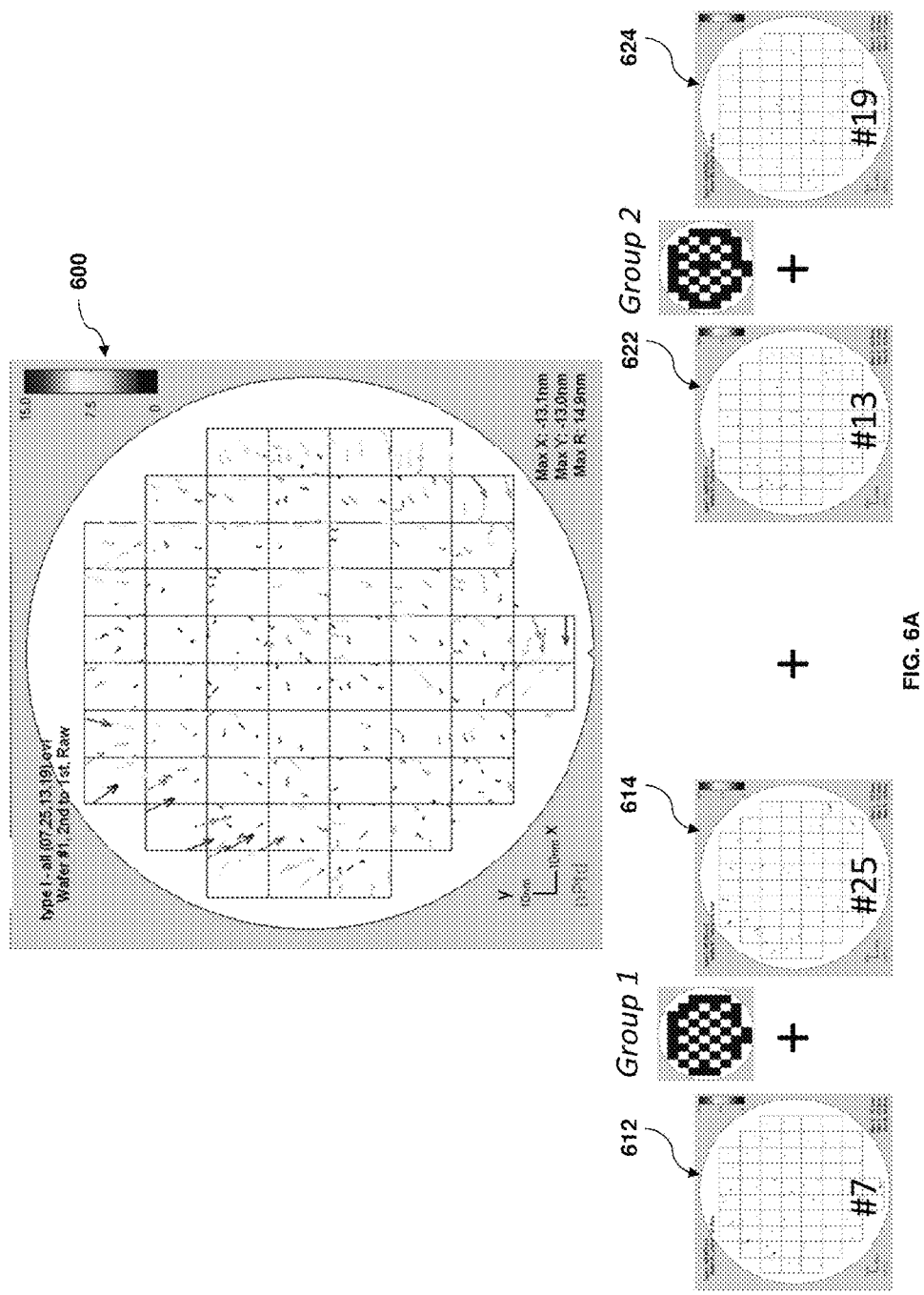
FIG. 6A is an exemplary combined overlay correction map after combining overlay correction maps of a plurality of selected wafers in a lot according to some embodiments of the present disclosure.

When all selected wafers have been measured, method 200 proceeds to operation 220 by generating a combined overlay correction map 600 as in FIG. 6A using the overlay correction maps of all the selected wafers in a lot. The combined overlay correction map may be used for overlay control and monitoring. For example, the combined overlay correction map may reflect a linear model of the error distribution, e.g. overlay shift along a certain direction, on the measured wafers. The linear model may be used to make adjustment to the exposing tool 106, so that the overlay error may be reduced in the future exposures. For example, if there is a linear increase of the overlay errors along a certain direction, compensation may be made to adjust the mismatching and/or misalignment problems raised between mask and wafer in the exposing tool 106. The subsequent wafers may be performed with a lithography process at operation 202 after the adjustment made to the exposing tool 106. The overlay errors of the subsequent wafers may be then monitored by operations 204-220 as discussed above.

FIG. 6A is an exemplary combined overlay correction map 600 after combining overlay correction maps of a plurality of selected wafers in one lot. A group of wafers are selected using the wafer selection model at operation 204, and a group of fields are selected using the field selection model at operation 206. For example, wafer #7 and wafer #25 are selected from a lot, and the first group of fields is selected for overlay error measurement. Wafer #13 and wafer #19 are selected from the same lot, and the second group of fields is selected for overlay error measurement. At least one point is selected from each selected field on each selected wafer using the point selection model at operation 210 of method 200. The overlay correction map 612 of wafer #7, overlay correction map 614 of wafer #25, overlay correction map 622 of wafer #13, and overlay correction map 624 of wafer #19 are formed and combined to generate the combined overlay correction map 600 as shown in FIG. 6A.

Figure 6B:
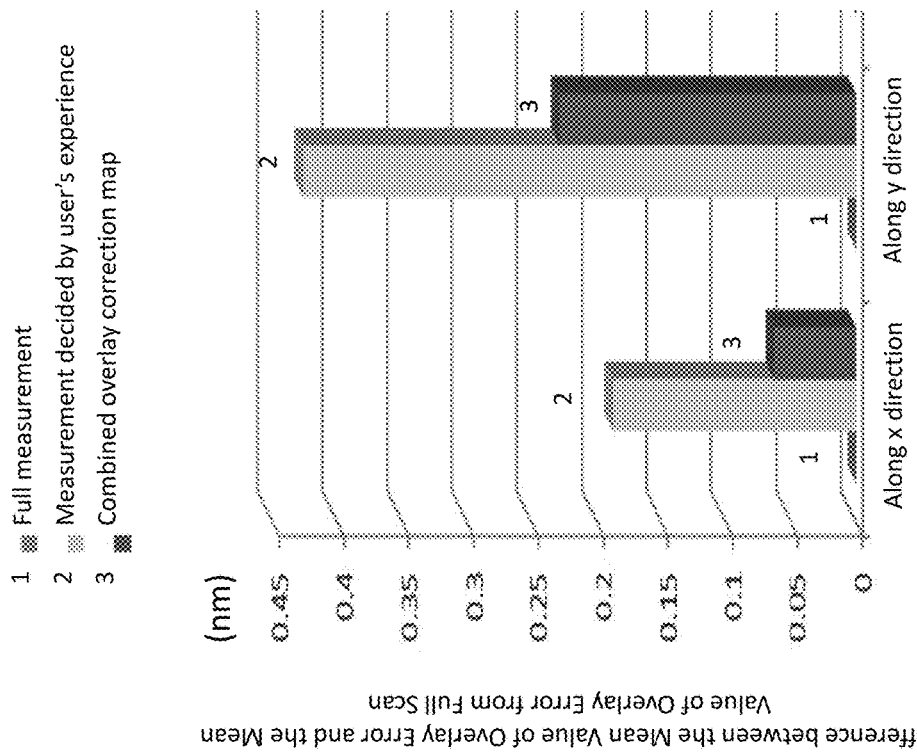
FIG. 6B illustrates the comparison results of the overlay errors measured using (1) a full measurement method, (2) an overlay measurement method decided by the user's experience, and (3) the combined overlay correction map according to some embodiments of the present disclosure.

FIG. 6B illustrates the comparison results of the overlay errors measured using (1) a full measurement method, (2) an overlay measurement method decided by the user's experience, and (3) the combined overlay correction map (e.g., 600 of FIG. 6A) using method 200 of FIG. 2A. The method 1 (full measurement) may include selecting 5 pieces of wafers out of one lot, selecting all 62 fields on each wafer, and selecting 2 random points in each field to perform the overlay measurement. The method 2 (overlay measurement decided by the user's experience) may include selecting 3 pieces of wafers out of one lot, selecting 17 fields out of 62 fields on each selected wafer, and selecting fixate 12 points in each selected field to perform the overlay measurement. The wafer selection, filed selection and point selection are all deiced by the user. The method 3 (overlay errors measured using the combined overlay correction map) may include selecting 7 wafers out of one lot using the wafer selection model disclosed at operation 204 of method 200, selecting first and second groups of fields using the field selection model disclosed at operation 206 of method 200, and selecting 8 fixate points in the center field, and selecting 2 points in the rest of the fields using the point selection model disclosed at operation 210 of method 200. The distance along x and y directions of each vector of the overlay errors measured in the above three measurement methods are respectively calculated. Geometric mean values of the overlay errors along x and y directions are then calculated, and the difference after comparing mean values of method 1 and 2, and method 1 and 3 are shown in FIG. 6B. As shown in FIG. 6B, the difference of the overlay errors mean values between method 3 and method 1 is less than the difference of the overlay errors mean values between method 2 and method 1. Therefore, method 3 is a more accurate and effective method for overlay monitoring and control compared to method 2.

Figure 7A:
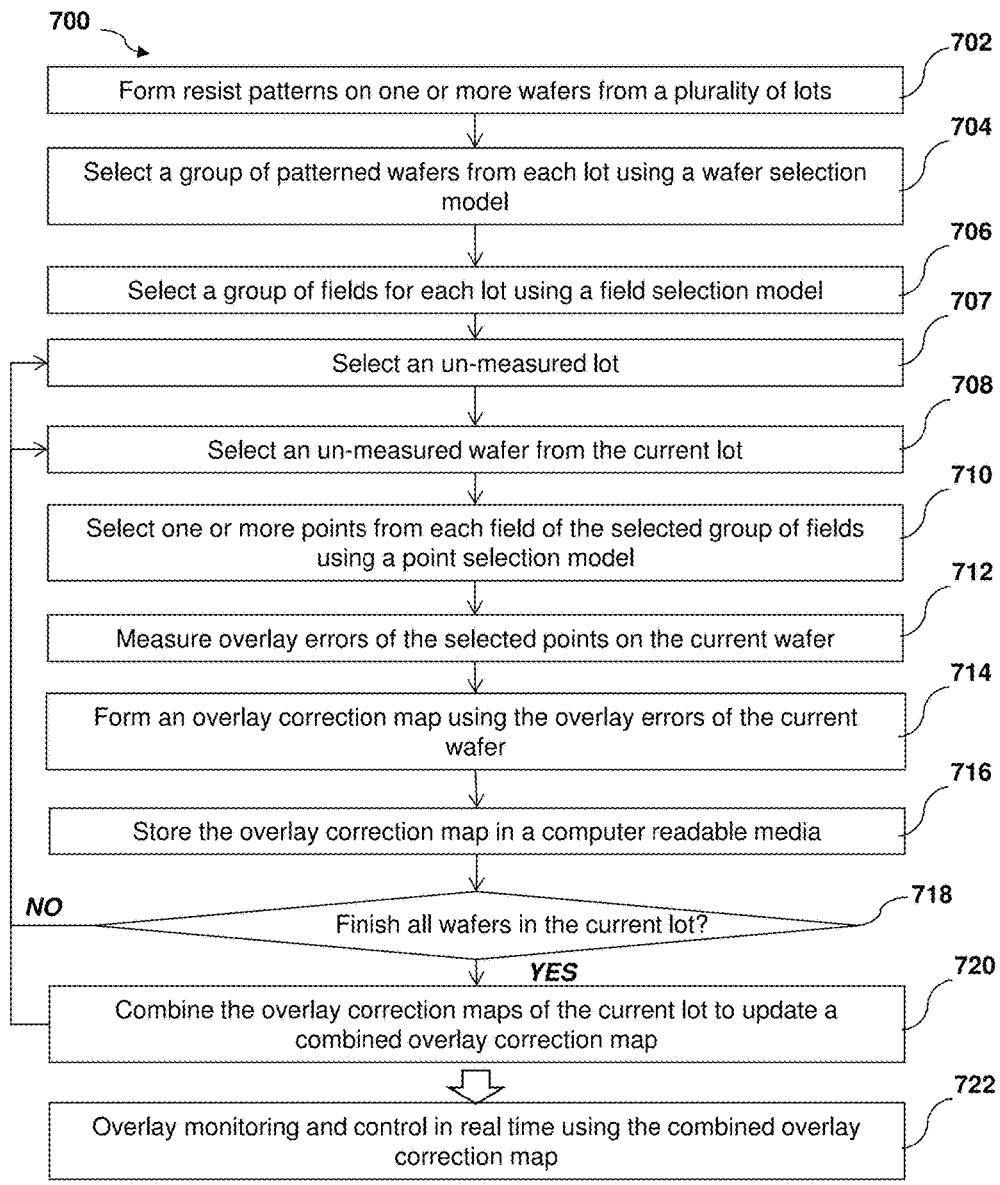
FIG. 7A is a flowchart illustrating a method for forming a combined overlay correction map for wafers from a plurality of lots according to various embodiments of the present disclosure.

The wafer selection model, field selection model and the point selection model discussed as above may be also used to form a combined overlay correction map from a plurality of lots for real time monitoring. FIG. 7A is a flowchart showing a method 700 for forming a combined overlay correction map for wafers from a plurality of lots according to various embodiments of the present disclosure. In some embodiments, the method 700 is implemented using the system 100 as shown in FIGS. 1A-1B. It is understood that additional steps can be provided before, during, and after the method 700, and some steps described can be replaced, eliminated, or moved around for additional embodiments of the method 700. The method 700 is an example, and is not intended to limit the disclosure beyond what is explicitly recited in the claims.

Method 700 starts with operation 702 by forming resist patterns on one or more wafers from a plurality of lots using the exposing tool 106 as shown in FIGS. 1A-1B. At operation 704, a group of patterned wafers are selected from each lot using a wafer selection model that is substantially similar to the wafer selection model discussed with regard to operation 204 in FIG. 2A. In some embodiments, the wafers selected from one lot may be different from the wafers selected from another lot.

Figure 7B:
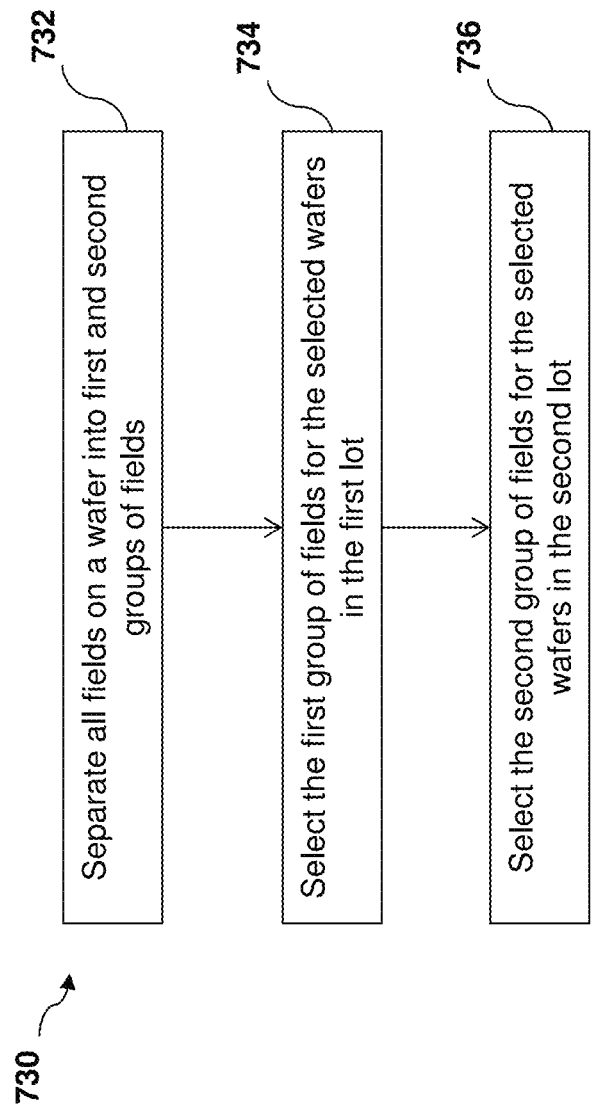
FIG. 7B is a flowchart illustrating an example of field selection model according to some embodiments of the present disclosure.
Figure 7C:
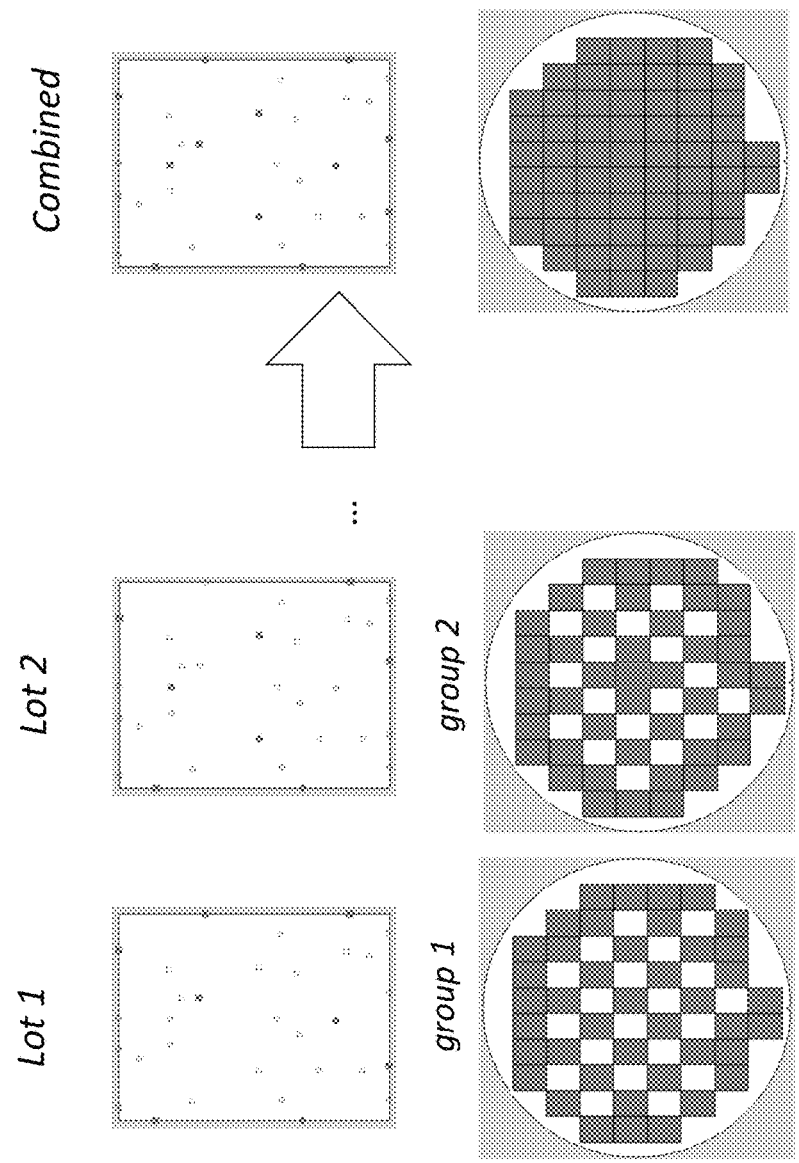
FIG. 7C illustrates a combined intra-field overlay map of point selection processes performed on wafers from a plurality of lots according to some embodiments of the present disclosure.

At operation 706, a group of fields may be selected for the wafers selected in each lot for the following overlay measurements. The fields may be selected using a field selection model 730 (as shown in FIG. 7B) that is substantially similar to the field selection model 400 discussed with regard to operation 206 of FIG. 2A and operation 402 of FIG. 4G. The filed selection model 730 starts with operation 732 by separating all fields on a wafer into first and second groups of fields, as shown in FIGS. 4E-4F. At operation 734 of the field selection model 730, the first group of fields is selected for all the selected wafers in the first lot as shown in FIG. 7C. At operation 736, the second group of fields is selected for all the selected wafers in the second lot as shown in FIG. 7C. Although only a group of fields is selected for the wafers in one lot, after combining the first and second lots, all fields have been measured for the wafers as shown in FIG. 7C.

Method 700 then proceeds to operation 707 by selecting an un-measured lot, and to operation 708 by selecting an un-measured wafer from the current lot. Method 700 proceeds to operation 710 by selecting one or more points from each field of the selected group of fields using a point selection model, to operation 712 by measuring overlay errors of the selected point on the current wafer, to operation 714 by forming an overlay correction map using the overlay errors of the current wafer, and to operation 716 by storing the overlay correction map in a computer readable media. Operations 710-716 may be substantially similar to operations 210-216 of method 200 with regard to FIG. 2A.

Method 700 proceeds to operation 718 by deciding if all the wafers in the current lot have been measured. When not all the wafers in the current lot are measured, method 700 proceeds to operation 708 by selecting the next un-measured wafer from the current lot.

When all the wafers in the current lot have been measured, method 700 proceeds to operation 720 by combining the overlay correction maps of all selected wafers in the current lot to update the combined overlay correction map. The combined overlay correction map may include overlay error information from a plurality of lots. The combined overlay correction map may be constantly updated after overlay measurement of each lot during the real time overlay monitoring and control.

After overlay measurement of one lot, operation 720 returns back to operation 707 to select the next un-measured lot to perform overlay measurements and form overlay correction maps for the next lot. The overlay correction maps of the next lot are then combined to be updated to the combined overlay correction map. In some embodiments, since the overlay correction maps generated from different lots may have different wafer, field, or point selections, and the wafers from different lots may be exposed under different conditions, the overlay correction maps may exhibit different scales with respect to, for example, error magnitude and/or error distribution. It may be difficult to directly combine the overlay correction data in the maps from different lots to form a combined overlay correction data. Therefore, an exponentially weighted moving average (EWMA) method may be used to correct and smooth the overlay correction maps from different lots. The overlay correction maps from different lots may then be combined to obtain the combined overlay correction map, as shown in FIG. 7C.

Operation 724 shows a real time overlay monitor and control using the up-to-date combined overlay correction map. The combined overlay correction map may be used to investigate the error distribution of the resist pattern on the wafer, thus corresponding adjustments can be made to the exposure tool 108 to offer better exposure accuracy in the future lithography process using the exposure tool 108.

Referring to the combined overlay correction map obtained using method 700 of FIG. 7A, in some embodiments, each overlay error may be represented using an arrow (for example as shown in FIG. 6A), where the length of the arrow reflects the distance between the positions of the selected point and the corresponding overlay mark. A length mean of the combined overlay error correction map may be calculated as the geometric mean value of all the overlay errors. Therefore the smaller number the length mean is, the less overlay error the map shows. The direction of the arrow is reflected by the angle between the arrow and a vertical direction, or between the arrow and a horizontal direction. An angle similarity may be calculated using a cosine function of the angle, and an angle similarity mean may be then calculated as the geometric mean value of all the overlay errors. Therefore the closer the angle similarity mean is to 1, the less overlay error the map shows. When comparing an overlay measurement method decided by the user's experience, and the combined overlay correction map obtained using method 700 of FIG. 7A, the length mean value of the combined overlay correction map is less than the length mean value of the overlay correction map decided by the user's experience. The angle similarity mean of the combined overlay correction map is greater than the angle similarity mean of the overlay correction map decided by user's experience. Therefore, the combined overlay correction map using method 700 is more accurate and effective for overlay monitoring and control compared to the overlay correction map decided by the user's experience.

Although the fields on a wafer are only described to be separated into two groups in the current disclosure, the fields may be divided into any suitable number of groups in any suitable topology, for example n groups. The lots to be measured to form the combined overlay correction map may also include m lots, where each of the n groups of fields is assigned to the selected wafers of each of the m lots for overlay measurement. The number m of the lots may or may not equal to the number n of the groups of the fields.

When the overlay measurement result is out of a predetermined specification on the combined overlay correction map obtained at operation 220 or operation 722, the patterned wafers may be fed back to the operation 202 or operation 702 to re-form the resist pattern on the unqualified wafers using an adjusted exposing condition and/or a corrected overlay shift. The method 200 or method 700 may be repeated for a plurality of times until the overlay measurement result is qualified for the specification.

When the overlay measurement result of resist pattern is within a predetermined specification at operation 220 or operation 722, the current exposing condition is qualified and the overlay shift is valid. The wafer with the resist pattern may be then sent on to one or more subsequent processes. The subsequent processes may include an implant process to form a well or a source/drain on the wafer. The subsequent processes may also include an etching process to transfer the resist pattern into the wafer, further forming various features on the wafer, such as isolation features or interconnection features.

The present disclosure provides a method for forming a combined overlay correction map for overlay control and monitoring. The method includes forming resist patterns on one or more wafers in a lot by an exposing tool; selecting a group of patterned wafers in the lot using a wafer selection model; selecting a group of fields for each of the selected group of patterned wafers using a field selection model; selecting at least one point in each of the selected group of fields using a point selection model; measuring overlay errors of the selected at least one point on a selected wafer; forming an overlay correction map using the measured overlay errors on the selected wafer; and generating a combined overlay correction map using the overlay correction map of each selected wafer in the lot. The method further includes forming a plurality of points in each field. The plurality of points correspond to overlay marks transferred from a mask to the formed resist patterns. The method further includes comparing positions of each selected point and corresponding overlay mark. Each overlay error is a vector including distance and angle differences between the positions of each selected point and the corresponding overlay mark.

In some embodiments, the wafer selection model includes weighting a wafer location in the lot using a weighting factor related to a possibility of wafer disposed in the wafer location being chosen for overlay measurement in previous measurements; and selecting a patterned wafer in the wafer location with a greatest weight factor. The weighting factor for the wafer location multiplies a number that is less than 1 as the wafer disposed in the wafer location gets chosen once for the overlay measurement. In some embodiments, the weight factor for the wafer location decreases exponentially when the wafer gets chosen once.

In some embodiments, the field selection model includes separating fields on a wafer into first and second group of fields, the first group of fields including center, edge and first type of fields, and the second group of fields including center, edge and second type of fields; separating the group of selected patterned wafers into first and second sub-groups of wafers; selecting the first group of fields for the first sub-group of the selected wafers; and selecting the second group of fields for the second sub-group of the selected wafers.

In some embodiments, the point selection model includes weighting points in each field using a weighting factor for each point related to a possibility of being chosen for overlay measurement in previous measurements; and selecting the at least one point in each field with a greatest weight factor. The weighting factor for the wafer location multiplies a number that is less than 1 as the wafer disposed in the wafer location gets chosen once for the overlay measurement.

In some embodiments, any of the wafer, field and point selection models is generated by a computer using data from previous measurements. The method further includes making compensation to the exposing tool using the combined overlay correction map.

In some embodiments, the method for forming a combined overlay correction map for overlay control and monitoring further includes forming resist patterns on one or more wafers in first and second lots by the exposing tool. The field selection model includes separating fields on a wafer into first and second group of fields, the first group of fields including center, edge and first type of fields, and the second group of fields including center, edge and second type of fields; selecting the first group of fields for the selected group of patterned wafers in the first lot; and selecting the second group of fields for the selected group of patterned wafers in the second lot. The combined overlay correction map is generated using the overlay correction map of each selected wafer in the first and second lots.

In yet some other embodiments, a method for forming a combined overlay correction map for overlay monitoring and control is disclosed. The method includes forming resist patterns on one or more wafers in each of first and second lots by an exposing tool; selecting a group of patterned wafers from each of the first and second lots using a wafer selection model; selecting a group of fields for the selected patterned wafers in each of the first and second lots using a field selection model; selecting at least one point in each of the selected group of fields using a point selection model; measuring overlay errors of the selected at least one point on a selected wafer; forming an overlay correction map using the measured overlay errors on the selected wafer; and generating a combined overlay correction map using the overlay correction map of each selected wafer in the first and second lots.

In yet some other embodiments, a system for overlay monitoring and control comprises an exposing tool configured to form resist patterns on one or more wafer in a lot; an overlay metrology tool coupled to the exposing tool; and a computer coupled to the overlay metrology tool. The overlay metrology tool is configured to select a group of patterned wafers in the using a wafer selection model, select a group of fields for each of the selected group of patterned wafers using a field selection model, select at least one point in each of the selected group of fields using a point selection model, and measure overlay errors of the selected at least one point on a selected wafer. The computer is configured to generate any of the wafer, field and point selection models, forming an overlay correction map using the measured overlay errors on the selected wafer, and generate a combined overlay correction map using the overlay correction map of each selected wafer in the lot.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A method for overlay monitoring and control, the method comprising:
   selecting a group of patterned wafers in a lot using a wafer selection model, each of the patterned wafers having a resist pattern formed thereon;
   selecting a group of fields for each of the selected group of patterned wafers using a field selection model;
   selecting at least one point in each of the selected group of fields using a point selection model;
   measuring overlay errors of the selected at least one point on a selected wafer;
   forming, by a processor, an overlay correction map using the measured overlay errors on the selected wafer;
   generating, by the processor, a combined overlay correction map using the overlay correction map of each selected wafer in the lot;
   determining a compensation for the overlay errors from the combined overlay correction map;
   implementing the compensation in an exposing tool to compensate for the overlay errors; and
   using the exposing tool and the implemented compensation, forming resist patterns on a subsequent group of wafers based on the combined overlay correction map.

2. The method of claim 1, further comprising:
   storing the overlay correction map in memory;
   retrieving the overlay correction map from memory; and
   retrieving, by the processor, at least one additional overlay correction map from memory, wherein the overlay correction map and the at least one additional overlay correction map are associated with wafers from the lot.

3. The method of claim 1, further comprising generating an updated combined overlay correction map using the previously generated combined overlay correction map and at least one overlay correction map from a patterned wafer from a different lot.

4. The method of claim 1, wherein the resist patterns include a plurality of points in each field of a plurality of fields, the plurality of points corresponding to overlay marks transferred from a mask in forming the resist patterns.

5. The method of claim 4, wherein the point selection model includes:
   selecting the at least one point which is different from a previous selected point.

6. The method of claim 4, wherein the point selection model includes:
   weighting points in each field using a weighting factor for each point related to a possibility of being chosen for overlay measurement in previous overlay measurements; and
   selecting the at least one point in each field with the greatest weighting factor,
   wherein the weighting factor for each point multiplies a number that is less than 1 as the point gets chosen once in the previous overlay measurements.

7. The method of claim 4, wherein measuring the overlay errors includes
   comparing positions of each selected point and corresponding overlay mark and wherein each overlay error is a vector including distance and angle differences between the positions of each selected point and the corresponding overlay mark.

8. The method of claim 1, wherein the field selection model includes:
   separating a plurality of fields on a wafer into first and second groups of fields, the first group of fields including center, edge and first type of fields, and the second group of fields including center, edge and second type of fields;
   separating the group of selected patterned wafers into first and second sub-groups of wafers;
   selecting the first group of fields for the first sub-group of wafers; and
   selecting the second group of fields for the second sub-group of wafers.

9. The method of claim 1, wherein any of the wafer, field and point selection models is generated by a processor using data from previous overlay measurements.

10. The method of claim 1, wherein the field selection model includes:
    separating fields on a wafer into first and second group of fields, the first group of fields including center, edge and first type of fields, and the second group of fields including center, edge and second type of fields;
    selecting the first group of fields for the selected group of patterned wafers in a first lot of wafers; and
    selecting the second group of fields for the selected group of patterned wafers in a second lot of wafers.

11. The method of claim 10, wherein the combined overlay correction map is generated using the overlay correction map of each selected wafer in the first and second lots.

12. The method of claim 1, wherein the wafer selection model is such that:
    the selecting of the group of patterned wafers is based on wafer position in the lot; and
    a likelihood of selecting a first patterned wafer in a wafer position is reduced by a previous selection of a second patterned wafer in the wafer position.

13. The method of claim 1, wherein the wafer selection model is such that:
    the selecting of the group of patterned wafers is based on wafer position in the lot; and
    a first likelihood of selecting a first patterned wafer in a wafer position is inversely proportional to a second likelihood of selecting a second patterned wafer in the wafer position in a previous selection.

14. The method of claim 1, wherein the field selection model is such that adjacent fields are in different groups.

15. A method for overlay monitoring and control, the method comprising:
    selecting a group of patterned wafers from each of a first lot of wafers and a second lot of wafers using a wafer selection model;
    selecting a group of fields for the selected patterned wafers in each of the first and second lots using a field selection model;
    selecting at least one point in each of the selected group of fields using a point selection model;
    measuring overlay errors of the selected at least one point on a selected wafer;
    forming, by a computer, an overlay correction map using the measured overlay errors on the selected wafer;
    generating, by the computer, a combined overlay correction map using the overlay correction map of each selected wafer in the first and second lots;
    determining a compensation adjustment for the overlay errors based on the combined overlay correction map; and exposing a subsequent group of wafers using the compensation adjustment.

16. The method of claim 15, wherein the field selection model includes:
    separating fields on a wafer into first and second group of fields, the first group of fields including center, edge and first type of fields, and the second group of fields including center, edge and second type of fields;
    selecting the first group of fields for the selected group of patterned wafers in the first lot; and
    selecting the second group of fields for the selected group of patterned wafers in the second lot.

17. A system for overlay monitoring and control, the system comprising:
    an overlay metrology tool configured to:
        select a group of patterned wafers from a lot using a wafer selection model,
        select a group of fields for each of the selected group of patterned wafers using a field selection model,
        select at least one point in each of the selected group of fields using a point selection model, and
        measure overlay errors of the selected at least one point on a selected wafer;
    a computer coupled to the overlay metrology tool and configured to:
        generate any of the wafer, field and point selection models,
        form an overlay correction map using the measured overlay errors on the selected wafer,
        generate a combined overlay correction map using the overlay correction map of each selected wafer in the lot; and
    an the exposing tool, wherein:
        the exposing tool is configured to form resist patterns on the one or more wafers in the lot;
        the exposing tool is configured to implement the adjustment during a lithographic exposure; and
        the overlay metrology tool is coupled to the exposing tool.

18. The system of claim 17, wherein each field includes a plurality of points that correspond to overlay marks transferred from a mask to the resist patterns using the exposing tool.

19. The system of claim 17, wherein the field selection model includes:
    separating fields on a wafer into first and second group of fields, the first group of fields including center, edge and first type of fields, and the second group of fields including center, edge and second type of fields;
    separating the group of selected patterned wafers into first and second sub-groups of wafers;
    selecting the first group of fields for the first sub-group of the selected wafers; and
    selecting the second group of fields for the second sub-group of the selected wafers.

20. The system of claim 17, wherein the point selection model includes:
    weighting points in each field using a weighting factor for each point related to a possibility of having been chosen in previous overlay measurements; and
    selecting the point in each field having the greatest weighting factor,
    wherein the weighting factor for each point multiplies a number that is less than 1 as the point gets chosen once in the previous overlay measurements.

* * * * *